United States Patent [19]

Jullien et al.

[11] 4,448,728
[45] May 15, 1984

[54] PREPARATION OF CIS ESTER-NITRILE CYCLOPROPANE COMPOUNDS

[75] Inventors: Renée Jullien, Palaiseau, France; Samir Benayache, Constantine, Algeria

[73] Assignee: Roussel Uclaf, Paris, France

[21] Appl. No.: 275,291

[22] Filed: Jun. 19, 1981

[30] Foreign Application Priority Data

Jun. 20, 1980 [FR] France ................. 80 13734

[51] Int. Cl.³ .................................... C07C 121/46
[52] U.S. Cl. .......................................... 260/464
[58] Field of Search ........................... 260/464

[56] References Cited

U.S. PATENT DOCUMENTS

| | | | |
|---|---|---|---|
| 3,397,223 | 8/1968 | Payne | 260/464 |
| 4,118,412 | 10/1978 | Cleare et al. | 260/464 |
| 4,174,348 | 11/1979 | Kramer et al. | 260/464 |
| 4,198,347 | 4/1980 | Punja | 260/464 |
| 4,211,720 | 7/1980 | Austermuhle-Bertola | 260/464 |
| 4,228,299 | 10/1980 | Ferguson et al. | 260/464 X |
| 4,284,582 | 8/1981 | Kaye et al. | 260/464 |
| 4,307,033 | 12/1981 | Hoffmann et al. | 260/464 |

FOREIGN PATENT DOCUMENTS

| | | |
|---|---|---|
| 2923778 | 12/1980 | Fed. Rep. of Germany . |
| 2371415 | 6/1978 | France . |
| 2281919 | 8/1979 | France . |
| 2355811 | 12/1980 | France . |

| | | | |
|---|---|---|---|
| 53-108951 | 9/1978 | Japan | 260/464 |

*Primary Examiner*—Joseph Paul Brust
*Attorney, Agent, or Firm*—Muserlian, Bierman, Bierman & Peroff

[57] ABSTRACT

Novel cyclopropane-1-carboxylic acid compounds of the formula

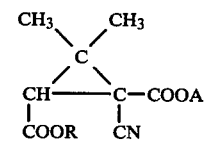

wherein CN and —COOR are in the cis position, A is selected from the group consisting of hydrogen and an alkali metal and R is alkyl of 1 to 4 carbon atoms and their preparation and a process for the preparation of a compound of the formula

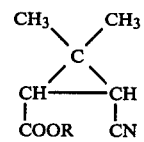

of cis configuration and R is alkyl of 1 to 4 carbon atoms.

6 Claims, No Drawings

PREPARATION OF CIS ESTER-NITRILE CYCLOPROPANE COMPOUNDS

STATE OF THE ART

French Pat. Nos. 2,281,919, 2,355,811 and 2,371,415 describe the decarboxylation of esters of cyclopropanecarboxylic acids different from those of formula I and the process is generally effected by heating in the presence of catalytic amounts of a metal halide or a metal cyanide. But the alkali metals salts are not decarboxylated nor is the configuration of the resulting compounds indicated and the compounds are believed to be mixtures of the cis and trans isomers. In any case, the said processes are not stereospecific.

OBJECTS OF THE INVENTION

It is an object of the invention to provide the novel compounds of formula I and a novel process for their preparation.

It is a further object of the invention to provide a novel stereospecific process for the preparation of the cis isomers of formula III.

These and other objects and advantages of the invention will become obvious from the following detailed description.

THE INVENTION

The novel compounds of the invention are cyclopropane carboxylic acid compounds of the formula

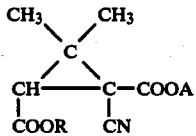

wherein CN and —COOR are in the cis position, A is selected from the group consisting of hydrogen and an alkali metal and R is alkyl of 1 to 4 carbon atoms.

Examples of A are hydrogen and alkali metals such as sodium, potassium or lithium and examples of R are methyl, ethyl, propyl, isopropyl and branched or linear butyl. Specific preferred compounds of formula I are 2,2-dimethyl-3-ethoxycarbonyl-1-cyano-cyclopropane-carboxylic acid with the ethoxycarbonyl and cyano being in the cis positions and its sodium and potassium salts.

The novel process of the invention for the preparation of the compounds of formula I comprises reacting a compound of the formula

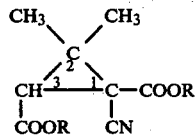

wherein the 3—COOR and —CN are in the cis positions and R is alkyl of 1 to 4 carbon atoms with an alkali metal saponification agent in an aqueous-alcoholic medium to obtain the corresponding alkali metal salt of formula I and optionally reacting the latter with an acid agent to obtain the compound of formula I wherein A is hydrogen which may be optionally salified with an alkali metal base to obtain the corresponding alkali metal salt of formula I.

In a preferred mode of the said process, the saponification agent is sodium hydroxide or potassium hydroxide and the reaction is effected in an aqueous lower alkanol such as aqueous methanol or aqueous ethanol. The acid agent is one of the usual strong acids.

The process of the invention is unexpected in the selectivity of the saponification since it could not be expected a priori that the saponification would effect only the ester group attached to the same carbon atom as the cyano group without effecting the second ester group present in the molecule. The process of the invention does not show any trace of the saponification of the second ester group occuring.

The compounds of formula I are useful to prepare known intermediate products and may, for example, be used to prepare compounds of formula III which are useful to prepare esters of the pyrethrinoid type having insecticidal activity as described in Japanese patent application No. 77-556 A/43.

In another process of the invention to produce compounds of the formula

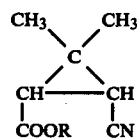

wherein —COOR and —CN are the cis positions and R is alkyl of 1 to 4 carbon atoms, a compound of formula I wherein A is an alkali metal is heated in an aprotic solvent at 100° to 150° C. in the presence of 1 to 4 moles of water per mole of the compound of formula I.

In a preferred mode of the said process, A is sodium or potassium and the aprotic solvent is selected from the group consisting of dimethylformamide, dimethylsulfoxide and dimethylacetamide. The heating is preferably effected at 120° to 140° C. for 2 to 6 hours.

The latter process of the invention for the preparation of the compounds of formula III is characterized in that the starting compound of formula I wherein A is sodium or potassium is directly obtained from saponification with sodium or potassium hydroxyde of a compound of formula II and then reacted to form the compound of formula III. This process permits to avoid the isolation of the compounds of formula I wherein A is hydrogen.

The latter decarboxylation process has the advantages over the prior art processes of leading to the desired cis isomeric compounds in yields on the order of 94% which is particularly advantageous as the cis compounds are the more important due to the greater insecticidal activity of the final insecticidal esters. The latter process permits to avoid degradation products due to the opening of the cyclopropane ring which is particularly to be feared, given the operating conditions of the process. The process leads to decarboxylation yields of up to 98% and to a total yields (saponification+decarboxylation) of the order of 88%.

The starting compounds of formula II are described in U.S. Pat. No. 3,397,223 or can be obtained according to the process of that said U.S. patent.

In the following examples there are described several preferred embodiments to illustrate the invention. However, it should be understood that the invention is not intended to be limited to the specific embodiments.

EXAMPLE 1

2,2-dimethyl-3-ethoxycarbonyl-1-cyano-cyclopropane-1-carboxylic acid

A mixture of 2 g of ethyl 2,2-dimethyl-3-ethoxycarbonyl-1-cyano-cyclopropane-1-carboxylate (prepared as in U.S. Pat. No. 3,397,223) and 4.71 g of 10% ethanolic potassium hydroxide was stirred under an inert atmosphere for 15 hours and the ethanol was then evaporated under reduced pressure. The residue was washed with ether and was then taken up in ether. The pH of the solution was adjusted to 3 by addition of dilute sulfuric acid and the decanted ether phase was washed with water, dried and evaporated to dryness under reduced pressure to obtain 1.6 g of 2,2-dimethyl-3-ethoxycarbonyl-1-cyano-cyclopropane-1-carboxylic acid with a melting point of $\simeq 130°$ C. (decomposition).

NMR Spectrum (deuteroacetone): Peaks at 1.29 ppm (triplet—3H J=7 Hz); at 1.37 ppm (singulet, 3H); at 1.54 ppm (singulet, 3H); at 2.63 ppm (singulet, 3H); at 4.2 ppm (quadruplet, 2H, J=7 Hz).

IR Spectrum (chloroform): Absorption at 2222 cm$^{-1}$ (—CN); at 1730 cm$^{-1}$ (C=O).

EXAMPLE 2

2,2-dimethyl-3-ethoxycarbonyl-cyclopropane-1-carbonitrile 0.5 g of the product of Example 1 was added at 0° to 5° C. to a suspension of 5.2 g of dimethylformamide and 0.094 g of sodium hydride as a 60% suspension in oil and the mixture was stirred until hydrogen evolution ceased. Then, 0.128 g of water were added thereto and the mixture was heated at 130° C. under an inert atmosphere for 5 hours and was then cooled. The mixture was poured into a mixture of 25 g of ice and 200 ml of ether with stirring and the decanted aqueous phase was extracted with ether. The combined ether phases were washed with aqueous sodium chloride solution, dried and evaporated to dryness to obtain 0.39 g of 2,2-dimethyl-3-ethoxycarbonyl-cyclopropane-1-carbonitrile. Gas chromatography showed the mixture contained 94% of the cis isomer and 6% of the trans isomer which mixture was chromatographed over silica gel and eluted with an 8—2 n-hexane-ethyl acetate mixture to obtain separately the expected cis isomer melting at 69° C., and the trans isomer.

NMR Spectrum (carbon tetrachloride): cis isomer—peaks at 1.27 ppm (singulet, CH$_3$); at 1.31 ppm (triplet, CH$_3$, J=7 Hz); at 1.42 ppm (singulet, CH$_3$); at 1.58–1.78 ppm (doublets, 2 CH, J=8 Hz); at 4.18 ppm (quadruplet, CH$_3$ J=7 Hz). trans isomer—peaks at 1.29 ppm (singulet, CH$_3$); at 1.3 ppm (triplet, CH$_3$, J=7 Hz); at 1.47 ppm (singulet, CH$_3$); at 1.88–2.0 ppm (doublets, 2 CH, J=5 Hz); at 4.14 ppm (quadruplet, CH$_2$, J=7 Hz).

IR Spectrum (carbon tetrachloride): cis isomer—Absorption at 2242 cm$^{-1}$ (—CN) and 1730 cm$^{-1}$ (—C=O). trans isomer—Absorption at 2237 cm$^{-1}$ (—CN) and at 1733 cm$^{-1}$ (—C=O).

EXAMPLE 3

2,2-dimethyl-3-ethoxycarbonyl-cyclopropane-1-carbonitrile

Using the procedure of Example 2, 0.237 g of 40% sodium hydroxide in place of sodium hydride and 0.128 g of water, a 98% yield of 2,2-dimethyl-3-ethoxycarbonyl-cyclopropane-1-carbonitrile was obtained in the form of a mixture of 89% of the cis isomer and 11% of trans isomer which could be separated as in Example 2.

EXAMPLE 4

2,2-dimethyl-3-ethoxycarbonyl-cyclopropane-1-carbonitrile

Using the procedure of Example 2, 5.6 g of dimethylsulfoxide were used in place of dimethylformamide to obtain a 95% yield of 2,2-dimethyl-3-ethoxycarbonyl-cyclopropane-1-carbonitrile in the form of a mixture of 88% of the cis isomer and 12% of the trans isomer which could be separated as in Example 2.

EXAMPLE 5

A mixture of 2 g of ethyl 2,2-dimethyl-3-ethoxycarbonyl-1-cyano-cyclopropane-1-carboxylate and 4.71 g of 10% ethanolic potassium hydroxide was stirred under an inert atmosphere for 15 hours and the ethanol was evaporated under reduced pressure. The resulting potassium salt was washed with ether and added to 5.2 g of dimethylformamide and 0.128 g of water. The mixture was heated at 130° C. under an inert atmosphere for 5 hours and the mixture was cooled and poured into a stirred mixture of 25 g of ice and 200 ml of ether. The decanted aqueous phase was extracted with ether. The combined ether phases were washed with aqueous sodium chloride solution, dried and evaporated to dryness to obtain 1.23 g of 2,2-dimethyl-3-ethoxycarbonyl-cyclopropane-1-carbonitrile in the form of a mixture of 90% of the cis isomer and 10% of the trans isomer which could be separated as in Example 2.

EXAMPLE 6

The process of Example 5 was repeated with the replacement of 10% ethanolic potassium hydroxide with 7% ethanolic sodium hydroxide to obtain an 88% yield of 2,2-dimethyl-3-ethoxycarbonyl-cyclopropane-1-carbonitrile as a mixture of 93% of the cis isomer and 7% of the trans isomer which could be separated as in Example 2.

Various modifications of the processes and products of the invention may be made without departing from the spirit or scope thereof and it is to be understood that the invention is intended to be limited only as defined in the appended claims.

What is claimed is:

1. A process for the preparation of a compound of the formula

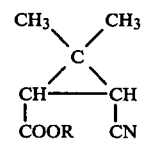

III wherein —COOR and —CN are in the cis positions and R is alkyl of 1 to 4 carbon atoms comprising heating a mono-ester, mono-salt, mono-nitrile compound of the formula

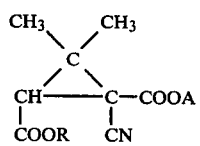

where R is alkyl of 1 to 4 carbon atoms and wherein —CN and —COOR are in the cis position and wherein A is an alkali metal in an aprotic solvent at 100° to 150° C. in the presence of 1 to 4 moles of water per mole of the said mono-ester, mono-salt, mono-nitrile.

2. The process of claim 1 wherein A is sodium or potassium.

3. The process of claim 1 wherein the aprotic solvent is selected from the group consisting of dimethylformamide, dimethylacetamide and dimethylsulfoxide.

4. The process of claims 1, 2 or 3 wherein the temperature is 120° to 140° C.

5. The process of claim 1 wherein the heating is effect for 2 to 6 hours.

6. A process for the preparation of a compound of the formula

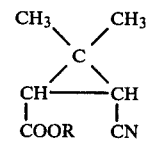

wherein —COOR and —CN are in the cis position and R is alkyl of 1 to 4 carbon atoms comprising saponifying a compound of the formula

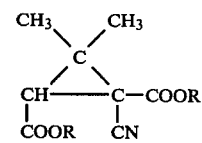

wherein —COOR and —CN are in the cis position and R is as above with an alkali metal saponification agent in an aqueous-alcoholic medium to obtain a compound of

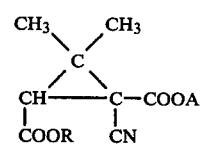

wherein R is as above, A is alkali metal and wherein —CN and —COOR are in the cis position, and heating the latter in the presence of 1 to 4 moles of water per mole of salt at 100° to 150° C. in an aprotic solvent.

* * * * *